United States Patent [19]
Unger et al.

[11] Patent Number: 5,610,322
[45] Date of Patent: Mar. 11, 1997

[54] DEVICE FOR PACKING CHROMATOGRAPHY COLUMNS

[75] Inventors: Bernhard Unger, Niedernhausen; Rainer Dickhardt, Kelkheim, both of Germany

[73] Assignee: Hoechst Aktiengesellschaft, Frankfurt am Main, Germany

[21] Appl. No.: 527,459

[22] Filed: Sep. 13, 1995

[30] Foreign Application Priority Data

Sep. 15, 1994 [DE] Germany .................. 44 32 887.7

[51] Int. Cl.⁶ .................. B01D 15/08; G01N 30/56; B65D 1/08
[52] U.S. Cl. .................. 73/23.39; 73/61.53; 210/198.2
[58] Field of Search .................. 73/23.39, 61.52, 73/61.53, 61.57, 23.42; 210/663, 670, 656, 635, 198.2; 96/101

[56] References Cited

U.S. PATENT DOCUMENTS

| | | | |
|---|---|---|---|
| 3,334,514 | 8/1967 | Catravis | 73/23.1 |
| 3,471,261 | 10/1969 | Patterson | 23/230 |
| 4,086,051 | 4/1978 | Srinivas | 432/198 |
| 4,361,482 | 11/1982 | Teetz et al. | 210/198.2 |
| 5,158,676 | 10/1992 | Kreher et al. | 210/198.2 |
| 5,167,809 | 12/1992 | Mann et al. | 210/198.2 |
| 5,169,522 | 12/1992 | Shalon et al. | 210/198.2 |
| 5,186,839 | 2/1993 | Kimura et al. | 210/656 |
| 5,192,433 | 3/1993 | Shalon | 210/198.2 |
| 5,213,683 | 5/1993 | Mann | 210/198.2 |
| 5,241,998 | 9/1993 | Ashraf-Khorassani | 141/67 |
| 5,378,359 | 1/1995 | Huse et al. | 210/198.2 |
| 5,378,360 | 1/1995 | Huse et al. | 210/198.2 |
| 5,378,361 | 1/1995 | Baeckström | 210/198.2 |
| 5,453,163 | 9/1995 | Yan | 204/180.1 |
| 5,482,628 | 1/1996 | Schick | 210/198.2 |

FOREIGN PATENT DOCUMENTS

| | | |
|---|---|---|
| 0049850B1 | 4/1982 | European Pat. Off. . |
| 0515955A3 | 12/1992 | European Pat. Off. . |
| 0515955A2 | 12/1992 | European Pat. Off. . |
| 62-11161 | 1/1987 | Japan . |

OTHER PUBLICATIONS

"BioProcess™ Glass Columns", Pharmacia LKB Biotechnology, No. 60–01–063, pp. 1–17 (1989).

*Primary Examiner*—Hezron E. Williams
*Assistant Examiner*—J. David Wiggins
*Attorney, Agent, or Firm*—Finnegan, Henderson, Farabow, Garrett & Dunner, L.L.P.

[57] ABSTRACT

A device, consisting of a chromatography column which is closed off at the top by a plunger and, at the bottom, by a connection piece and has one or more lateral openings in the upper part, a container that contains suspended chromatography material and is connected via a line to one or more of the lateral openings, and a container that contains packing medium and is connected via a line to one or more of the lateral openings and/or is connected via a line to the plunger, is suitable for packing a chromatography column. A method for producing chromatography packings with the aid of the device is described.

9 Claims, 2 Drawing Sheets

DEVICE FOR PACKING CHROMATOGRAPHY COLUMNS

The invention relates to a device for packing chromatography columns, a pressure chromatography device contained therein and a method for producing chromatography packing.

Known methods for packing chromatography columns include filling with rigid or soft sorbents present in suspension, with subsequent compressing of the sorbents with the aid of a constant volume flow of the packing medium (Pharmacia LKB Biotechnology, Bioprocess® Glass columns, No. 60-01-063 (1989)). A further method consists in axially compressing and consolidating the filled chromatography material by loading a mobile plunger (EP 0 049 850). Disadvantages of the known methods are:

accurate matching of solvent or solvent mixtures to the sorbent to be packed (not every sorbent can be suspended and compacted with any desired solvent);

the exact volume/weight relationship of solvent and sorbent for formation of a defined packing height (the packing height correlates with the added amount of sorbent and must be accurately established beforehand in numerous experiments);

the emissions which take place when using toxic organic solvents, which must frequently be handled directly;

the sometimes very elaborate assembly work before or after the packing process;

the high hydraulic pumping powers which are necessary for compacting rigid sorbents;

the overall height of the apparatus.

The invention is intended to remedy these drawbacks. The invention, as it is explained in the claims, achieves the object with a chromatography column which is closed off at the top by a plunger and, at the bottom, by a connection piece and has one or more lateral openings in the upper part, a container that contains suspended chromatography material and is connected via a line to one or more of the lateral openings, and a container that contains packing medium and is connected via a line to one or more of the lateral openings and/or is connected via a line to the plunger.

Packing of the chromatography column is achieved by filtration. In this case a packing medium—as a rule the liquid for suspending the chromatography material (sorbent)—flows through the chromatography column which is completely filled with packing medium. The plunger is in this case located above the lateral opening(s). In this case the packing medium leaves the chromatography column via the connection piece and can be fed back via a line into the container for the packing medium and then into the chromatography column or is discharged into a collection vessel. The packing medium can flow via the fixed or mobile plunger, through one or more of the lateral openings or simultaneously through the fixed or mobile plunger and the lateral openings into the chromatography column. The total volume flow of the packing medium is distributed between the plunger and the lateral openings, for example by 10:90 to 40:60, preferably by 20:80 to 30:70, in particular 25:75.

The chromatography material is supplied only via the lateral openings. The supply rate of the chromatography material is variable and depends on the concentration of the suspended material and the pumping power of the pump.

After sedimentation of a small amount of sorbent on the bottom frit of the chromatography column (this is part of the connection piece) a back-pressure which serves for optimum compaction of the chromatography packing, is set up inside the column. This pressure remains throughout the packing process and depends on both packing height and volume flow. By pressure-dependent adjustment of the delivery rate of the circulation pump (or packing pump), the pressure can always be maintained at a particular level, until the column has been filled with the entire sorbent suspension. The packing height can be defined by the quantity of suspended sorbent and matched to requirements during the packing process.

The advantages obtained through the invention essentially consist in that, apart from a brief initiation phase, in which a sediment must first be built up on the bottom frit of the column, the chromatography packing is always produced under the same filtration pressure; as a result of the pressure drop in the chromatography packing, a plane surface is produced during the filtration process and the density distribution of the chromatography packing is homogeneous.

Further advantages with the same packing process are found in the relatively short column design, the emission-free operation mode, the possibility of automating the process and avoiding assembly work, during or after packing, which is very elaborate in the case of systems having large dimensions. Devices, such as the elution pump necessary for chromatography, which are present can furthermore be integrated in the packing process.

After packing, the plunger is lowered onto the chromatography packing below the lateral column openings, the remaining suspension either being pushed through the chromatography packing or emerging from the chromatography column via the frit in the plunger. The lateral openings are closed off during chromatography.

The chromatography columns that can be used are, for example, cylindrical columns with round or oval cross-sections; the material of the columns is, for example, glass, plastic or steel.

The plunger contains devices for fastening the packing medium supply from the container, seals and a filter, for example a sintered plate or a net. Steel or plastics such as polypropylene or fluoroethenepropene are suitable as material. The chromatography packing consists of the materials, for example silica gel, agarose, polyacrylamide, hydroxyapatite, diethylaminoethyl cellulose or cellulose, that are suitable for chromatography processes.

All known liquid-chromatography liquids such as water, buffer or organic solvent may constitute the packing medium. The lateral openings are located in the upper part of the chromatography column. The number of openings depends on the diameter of the column. With a column diameter of 30 cm, 3 to 6 openings have proved expedient. The diameter of the lateral openings corresponds to the diameter of the supply lines. The openings can be closed during the chromatography.

The connection piece closes off the chromatography column at the bottom, and contains a plane filter element, for example a sintered plate, on which the sorbent material forms a sediment, a connection opening for connection of lines as well as, optionally, further supports for the chromatography column.

Figure 1:
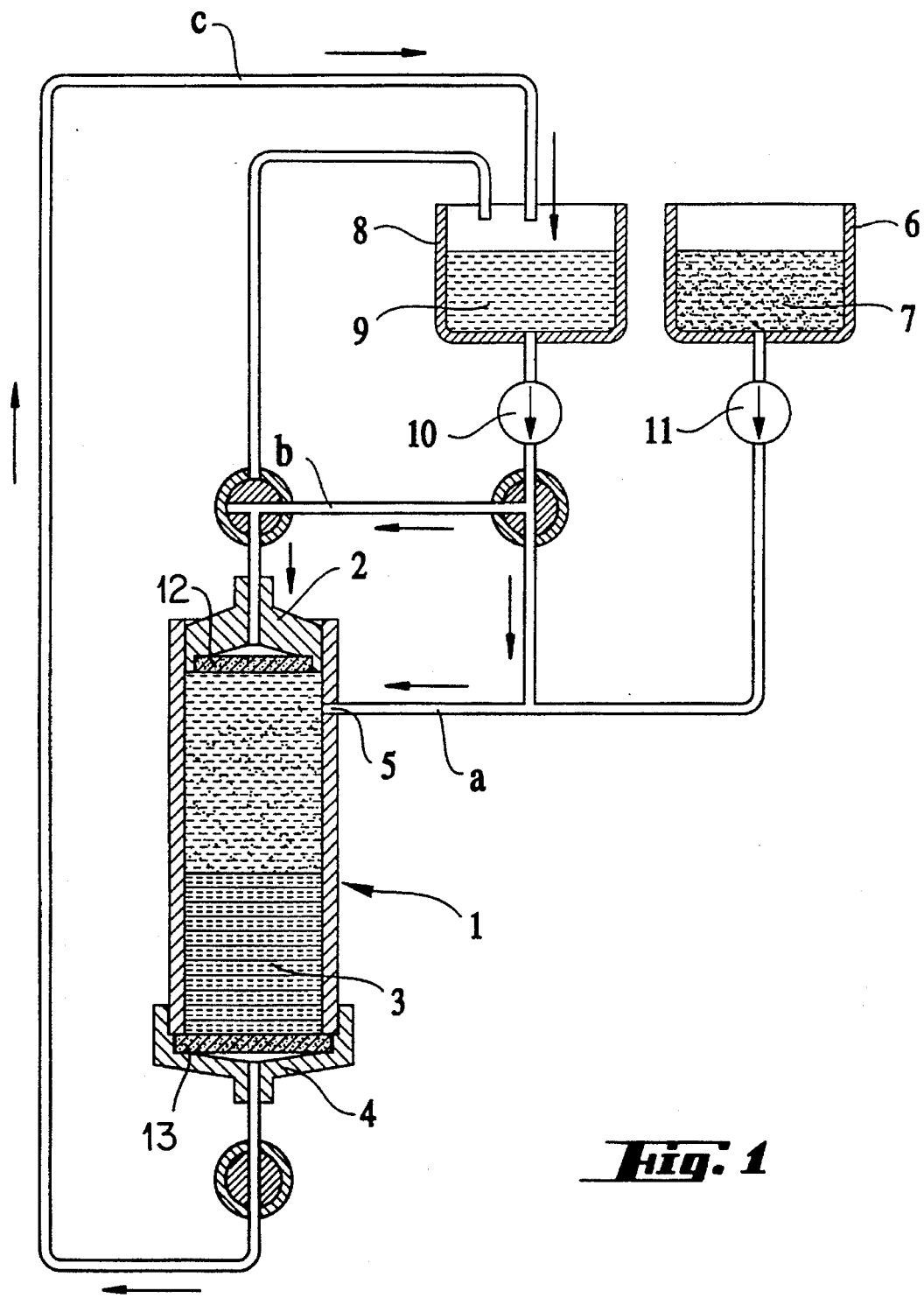
FIG. 1 is a schematic view of the instant invention during formation and growth of a gel bed of chromatography packing.

The device represented in FIG. 1 is a particular embodiment which comprises a chromatography column (1) (See FIG. 1) which is closed off at the top by a plunger (2) and, at the bottom, by a connection piece (4), and has one or more lateral openings (5) in the upper part, a container (6) that contains suspended sorbent material (7) and is connected via the line (a) to one or more of the lateral openings (5), and a container (8) that contains packing medium (9) and is connected via the line (a) to one or more of the lateral openings (5) and/or via the line (b) to the plunger (2).

The invention furthermore relates to a method for producing chromatography packing (3), wherein a liquid packing medium is fed continuously into a chromatography column (1), the chromatography column being closed off at the top by a plunger (2) and, at the bottom, by a connection piece (4) and one or more lateral openings (5) being present in the upper part of the chromatography column, the supply of said packing medium taking place through the plunger and one or more lateral openings, the chromatography material being fed, with said packing medium, into the chromatography column via one or more lateral openings and the packing medium being discharged through an aperture in said connection piece.

The invention also relates to a pressure chromatography device, which comprises a chromatography column (1) which is closed off at the top by a plunger (2) and, at the bottom, by a connection piece (4), chromatography packing (3) obtainable through the method according to the invention for producing chromatography packing and which has one or more lateral openings (5) above said chromatography packing.

The invention also relates to chromatography packing (3) obtainable through the method according to the invention.

The invention will be explained in more detail hereafter with the aid of examples:

EXAMPLE 1

Preparation of the chromatography column for packing A cleaned bottom frit (13) is first of all provided with the corresponding new O-ring and mounted on the connection piece (4) removed from the column. A piston frit (12) is then fastened on the plunger (2) removed from the column. After reinstallation of the plunger back into the chromatography column, the plunger is next raised until it is above the lateral column openings (5). The lower connection piece (4) is firmly fitted by screws to the column tube in order to close the column.

Packing the Chromatography Column

In order to make it possible to pack the column (diameter 30 cm, height 1 m), from 300 to 500 l of n-propanol (packing medium (9) are introduced into the packing-material receiver or container (8).

Figure 2:
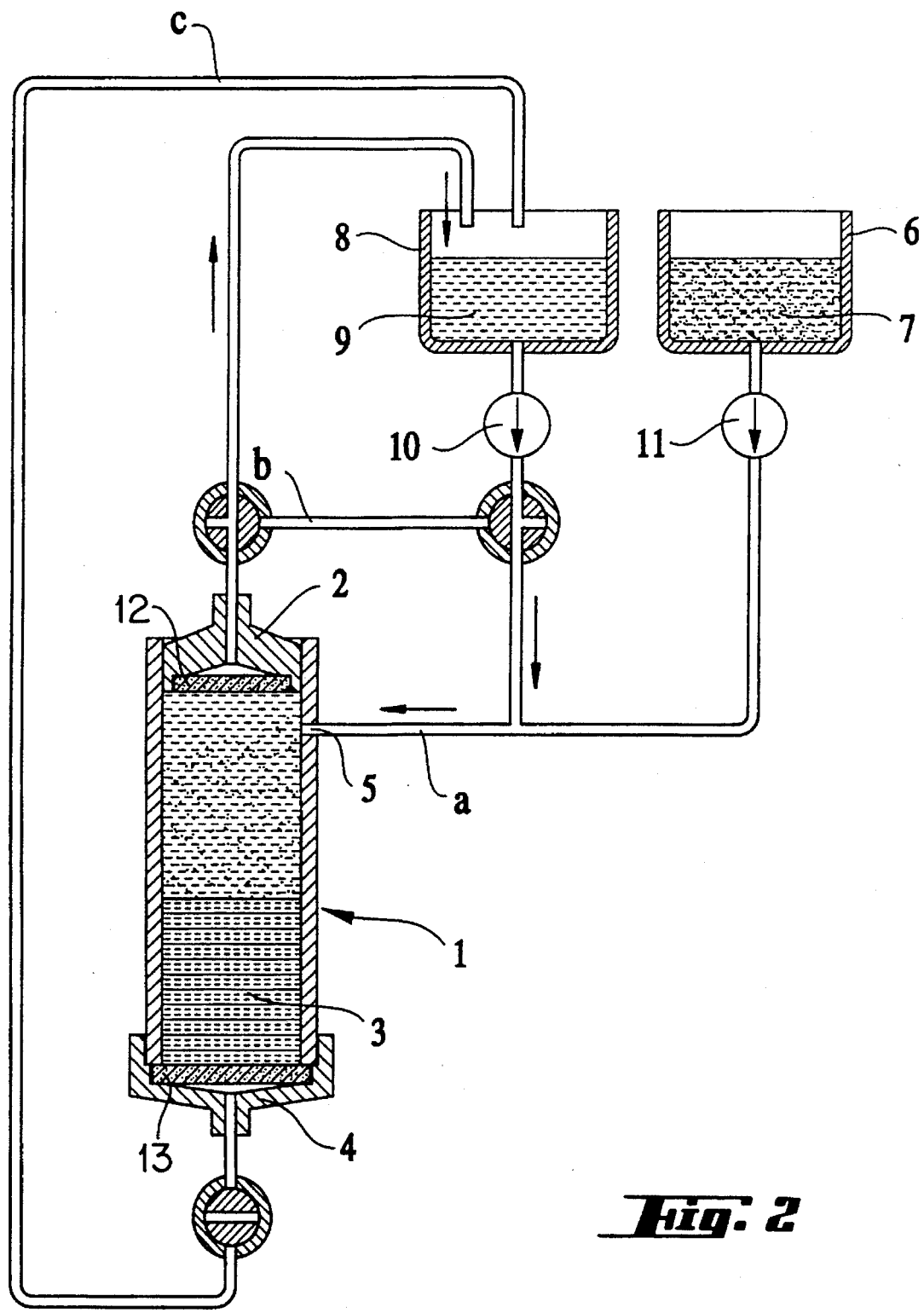
FIG. 2 is a schematic view of the chromatography column used in the instant invention during compaction of the chromatography packing using the packing pump alone.

The chromatography column (1) is then flooded with 100% n-propanol from the packing-material receiver (8) using the packing pump (10) with the column outlet (14) closed (FIG. 2). This is done in order to displace the air in the column tube through the piston frit into a collection vessel (not shown). As soon as uniform flow of n-propanol is established in the attached tube, the packing pump should be switched off.

100 l of n-propanol is then introduced into the container (6) and 12.5–13.5 kg of reverse-phase silica gel (RP silica gel; for example Kromasil C-8) is added under agitation then suspended for 14–16 minutes.

After the column outlet has been opened, the packing pump (10) pumps the packing medium (9) through the three lateral column openings (5) (only one is shown in FIG. 1), and through the piston frit (12) into the chromatography column (1), through the bottom frit (13) and the line (c) in the circuit.

The suspended RP silica gel (7) is slowly added to this solvent circuit with the aid of the pump (11). The mixture of silica gel and n-propanol is fed via the packing line (a) into the chromatography column (1).

A bed of gel accumulates slowly in the latter and the back pressure in the column increases to at most 85 bar. Through continuous reduction of the circuit volume flow, the pressure in the column is kept constant during growth of the gel bed. Keeping the pressure drop constant results in uniform formation of the chromatography packing (3). The suspended silica gel continues to be added until the desired gel bed height has been obtained, or the entire silica gel suspension has been pumped into the column. The chromatography packing is finally compressed for a further 30–35 minutes using the packing pump (10) by pumping through n-propanol (FIG. 2). The packing pump (10) is then turned off and the lateral openings (5) are closed. The plunger (2) is then lowered onto the surface of the gel.

EXAMPLE 2

Quality Assessment of the Column Packing 7.5 ml of a phenol/cresol test mixture and 40 ml of acetone are dissolved in 100 ml of methanol/water mixture (ratio 1:3). This solution is pumped into the chromatography column of Example 1 and then isocratically eluted with an n-propanol/water mixture. Three peaks occur on the elution diagram, from which the separation efficiency and the plate number of the column packing can be calculated.

We claim:

1. A method for producing chromatography packing, wherein a liquid packing medium is fed continuously into a chromatography column to be filled with a chromatography material, the chromatography column being closed off at the top by a movable plunger having a passageway formed therethrough and, at the bottom, by a connection piece, and one or more lateral openings being present in the upper part of the chromatography column, supply of said packing medium taking place through the passageway of the plunger and the one or more lateral openings, the chromatography material being fed at a controlled rate, with said packing medium, into the chromatography column via the one or more lateral openings and the packing medium being discharged through an outlet in said connection piece.

2. The method as claimed in claim 1, wherein the packing medium used is fed by a pump in a volume flow circuit through the chromatography column.

3. The method as claimed in claim 1, wherein the pressure at which the packing medium is fed into the chromatography column is constant.

4. The method as claimed in claim 1, wherein from 10% to 40% of the packing medium is fed via the plunger passageway and from 90% to 60% is fed via the one or more lateral openings into the chromatography column.

5. A pressure chromatography device, which comprises a chromatography column which is closed off at the top by a plunger and, at the bottom, by a connection piece, chromatography packing obtainable according to claim 1, and one or more lateral openings above said chromatography packing.

6. Chromatography packing obtainable by the method according to claim 2.

7. A device for packing a chromatography column, comprising:

a chromatography column closed at one end by a movable plunger having an opening therethrough, the chromatography column having at least one lateral opening in an upper portion of the chromatography column;

a first container containing a sorbent material and in flow communication with the at least one lateral opening in the chromatography column;

a second container containing a packing medium and in flow communication with the at least one lateral opening of the chromatography column and the plunger opening;

means for selectively supplying the sorbent material into the chromatography column via the at least one lateral opening; and means for selectively supplying the packing medium to the chromatography column through the at least one lateral opening and the plunger opening.

8. The device of claim 7, wherein the bottom of the chromatography column includes an outlet through which the packing medium is discharged.

9. The device of claim 7, wherein each of the supplying means comprises a pump.

* * * * *